US008281515B2

(12) United States Patent
Nichols et al.

(10) Patent No.: US 8,281,515 B2
(45) Date of Patent: Oct. 9, 2012

(54) METHODS FOR GROWING AND HARVESTING ALGAE AND METHODS OF USE

(75) Inventors: Everett J. Nichols, Edmonds, WA (US); James R. Scott, Bellevue, WA (US)

(73) Assignee: HaloSource, Inc., Bothell, WA (US)

( * ) Notice: Subject to any disclaimer, the term of this patent is extended or adjusted under 35 U.S.C. 154(b) by 0 days.

(21) Appl. No.: 12/824,948

(22) Filed: Jun. 28, 2010

(65) Prior Publication Data
US 2011/0016773 A1   Jan. 27, 2011

Related U.S. Application Data

(60) Provisional application No. 61/220,942, filed on Jun. 26, 2009.

(51) Int. Cl.
*A01G 7/00* (2006.01)
*A01H 13/00* (2006.01)
(52) U.S. Cl. .......................................... 47/1.4; 435/420
(58) Field of Classification Search .................. 435/420; 800/296; 47/1.4
See application file for complete search history.

(56) References Cited

U.S. PATENT DOCUMENTS

| 5,204,452 | A | 4/1993 | Dingilian |
| 5,336,415 | A | 8/1994 | Deans |
| 5,362,717 | A | 11/1994 | Dingilian |
| 5,726,123 | A | 3/1998 | Heinsohn |
| 6,407,040 | B1 | 6/2002 | Nichols |
| 6,821,427 | B2 | 11/2004 | Macpherson |
| 7,157,009 | B2 | 1/2007 | Nichols |
| 7,790,042 | B2 | 9/2010 | Nichols |
| 2010/0081835 | A1 | 4/2010 | Wu |

FOREIGN PATENT DOCUMENTS
JP   2008173010 A   *  7/2008

OTHER PUBLICATIONS

Knuckey, R.M., et al., "Production of Microalgal Concentrates by Flocculation and Their Assessment as Aquaculture Feeds," Aquacultural Engineering 35(3):300-313, Oct. 2006.
Morales, J., et al., "Harvesting Marine Microalgae Species by Chitosan Flocculation," Aquacultural Engineering 4(4):257-270, 1985.

* cited by examiner

*Primary Examiner* — Kent L Bell
(74) *Attorney, Agent, or Firm* — Christensen O'Connor Johnson Kindness PLLC

(57) ABSTRACT

Methods for increasing the growth and biomass of algae and algae lipids by growing the algae in the presence of a polycationic substance such as soluble or insoluble chitosan and/or chitin are disclosed. Also disclosed are methods of harvesting algae from an aqueous environment by growing the algae in aggregated clumps and/or mats (formed by the inclusion of soluble or insoluble chitosan and/or chitin or other polycationic or cationic substances) that can be easily removed from the aqueous environment either by filtration, surface skimming, and/or growing in a porous containment device, such as a natural or synthetic fabric, and removing the fabric from the aqueous environment containing the aggregated algae. The methods disclosed have direct applications in biofuel and energy production, agricultural feedstock production, nutrient production, greenhouse gas reduction, removal of microconstituents from water, and water reclamation.

33 Claims, 13 Drawing Sheets
(6 of 13 Drawing Sheet(s) Filed in Color)

METHODS FOR GROWING AND HARVESTING ALGAE AND METHODS OF USE

CROSS-REFERENCE TO RELATED APPLICATION

This application claims the benefit of U.S. Provisional Application No. 61/220,942, filed on Jun. 26, 2009, which is expressly incorporated herein in its entirety by reference.

BACKGROUND

Microalgae is a source of biofuels that offers an alternative to the use of conventional fossil fuels. Microalgae are primitive plants that grow in aqueous suspensions. Microalgae include single-celled photosynthetic microorganisms that utilize energy from sunlight to combine water and carbon dioxide to produce biomass that can contain significant quantities of lipids similar to that found in vegetable oils. The lipid material can be used in the production of biofuels through the chemical process known as transesterification. Reproduction of microalgae is primarily through asexual cell division, however, under certain growth conditions, sexual reproduction can occur. There are a number of groups of algae with thousands of known species. Some of the major classes studied for generation of algal biofuels are: the Diatoms; Green Algae; Golden-Brown Algae; Prymnesiophytes and the Eustigmatophytes.

A significant body of research demonstrates that photosynthetic microalgae can be propagated in open raceway ponds or in photosynthetic bioreactors and harvested for biofuel production. Microalgae have also been cultivated in the dark by fermentation to produce biofuel. Microalgae form storage lipids primarily in the form of neutral triglycerides that can be used to produce biodiesel through transesterification using alcohol and an acid or base as a catalyst.

The successful commercialization of microalgae as a biofuel source depends on a number of factors. The most significant are increased lipid (oil) yield and/or biomass growth enhancement and cost efficient harvesting methods.

A number of studies demonstrate that nutrient limitation such as nitrogen and/or silicon deprivation can induce algae to increase their lipid content. The downside to nutrient deprivation is a cessation of cell division and cell growth and the corresponding limitation of biomass such that the net yield on lipid production is not significant.

Further, the cost of harvesting microalgae from an aqueous environment is a limitation to successful commercialization of microalgae as a biofuel. One method for harvesting algae uses a microstrainer to screen out the algae. In this method, the water containing the suspended microalgae from an open raceway pond flows over a rotating or fixed microstrainer to collect the algae while the water passes through. The microalgae that is collected on the microstrainer is swept off by a moving scraper or backwashed and collected for centrifugation to concentrate the algae for extraction of the lipids.

Another method of harvesting microalgae involves allowing microalgae cultures to settle under the influence of polymers and $FeCl_3$. The high doses used and the high cost of flocculants (2-6 g/kg for organic flocculants and 15-200 g/kg for $FeCl_3$) combined with the high cost of cross-flow filtration used for harvesting is commercially undesirable. Other variants of the method involve centrifugation of the settled algae, which is also impractical and expensive.

Another method for harvesting microalgae is chemical flocculation followed by dissolved air flotation. The lipid contents were low for the flocculated algae harvested by dissolved air flotation compared to sedimented algae harvested by centrifugation.

Collection of algae by filtration over a bed of sand is another method for harvesting microalgae, but is not practical due to the difficulty and cost associated with removing the collected algae from the sand bed.

In view of the foregoing problems with conventional methods for growing and harvesting microalgae, it would be desirable to provide a method to enhance the growth rate of algae and/or increase the lipid content of algae without inhibiting cell division and that further allows effective harvesting.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

This disclosure relates to a method of growing and harvesting algae by introducing an effective amount of chitosan to an environment suitable for growing algae, such that the chitosan causes increased algae growth and, can also result in aggregated algae and/or mats of growing aggregated algae. The method advantageously results in algae that can be harvested more readily when aggregated by chitosan. The use of chitosan results in an increase in the growth of algae and may increase the lipid quantity in algae. The algae and lipids can be used as a source for biofuels, specialty chemicals, animal and fish feed, nutrients, ethanol production, biomass recovery useful for agriculture, and energy generation, such as methane combustion and ethanol production.

In the disclosed method, the environment suited for growing algae may contain an effective amount of soluble chitin and/or soluble chitosan, and, optionally, an anionic polymer, such as xanthan gum, alginate, carrageenan, carboxymethylcellulose or anionic polyacrylamide. Polycationic substances besides chitosan and chitin may also exhibit the same effects on algae growth and lipid yield and/or aggregated or mat-like growth. Such polycationic substances include: polycationic acrylamide; cationic guar; cationic starch; certain polyamines and other natural or synthetic cationic polymers.

Cultivating algae under conditions that include chitosan and/or chitin, and, optionally, an anionic polymer, the algae can grow in aggregated clumps and/or mats that are stable to dissociation under normal growth conditions. The cultivation of algae in the presence of chitosan or chitin alone or in combination with an anionic polymer, such as an anionic polysaccharide like xanthan gum, alginate, or carrageenan, advantageously increases the growth of the microalgae and may also increase lipid production of the microalgae.

In one embodiment of the invention, the chitosan-aggregated or chitosan-anionic polymer aggregated microalgae can be grown in a porous containment device (examples include synthetic and non-synthetic woven and non-woven fabrics) within an aqueous environment making harvesting easier by simply removing the containment device containing the aggregated/clumped/mat of algae from the water and pressing to a paste-like consistency using a belt press. The porous containment device (containing the aggregated or mats of growing microalgae) can be moved throughout the aqueous environment to bring the algae closer to a source of light energy, such as the sun. Alternatively, the containment device could be moved away from the source of light energy in order to provide diffuse light to protect the microalgae from the intensity of the light energy.

Another embodiment of the invention comprises growing the chitosan-aggregated or chitosan-anionic polymer aggregated microalgae in a raceway pond containing blocked holes provided throughout the bottom of the raceway. Harvesting the matted or aggregated microalgae can be accomplished by opening the holes covered by sliding plates and allowing the water to drain out into a containment pond positioned below the raceway pond containing the matted or aggregated microalgae. The aggregated microalgae are large enough so as not to pass through the holes and will remain in the drained raceway. The aggregated microalgae in the drained raceway pond can then be collected from the raceway pond using a moving scraper or spatula device configured to fit the contour of the raceway bottom. The collected water in the containment pond below can be pumped back into the raceway after the holes are closed by sliding the plate covers back in place.

Another embodiment of the invention comprises growing the chitosan-aggregated or chitosan-anionic polymer aggregated microalgae in a raceway pond that is gently sloped on one end to allow drainage during harvesting. The lower end could contain a drain covered by a strainer to prevent the aggregated or matted microalgae from passing into the drain and is capable of being opened and closed at will.

The use of chitosan and/or chitin to grow algae may provide an increase in the synthesis of the enzyme Acetyl CoA Carboxylase (ACCase), a key enzyme for catalyzing the synthesis of oils in microalgae, and thereby increasing the production of lipids.

The use of chitosan and/or chitin to grow algae may provide increased utilization of carbon dioxide by the microalgae and thereby provide increased carbon credits that can help to offset the cost of production.

Chitosan and/or chitin may be used to influence the chlorophyll and/or carotenoid pigment content and/or the light harvesting molecules used in photosynthesis content and/or their ratios in algae such that photosynthesis and/or growth under various light conditions can be optimized and/or lipid synthesis increased. By selecting the amount of chitosan in the growing environment, the chlorophyll content of the microalgae can be controlled and may be reduced or increased, depending on the amount of chitosan.

Chitosan and/or chitin may be used for decoupling the dependency of microalgae growth on light as an energy source. Chitosan, chitin, and/or other cationic substances can be used to influence microalgae growth without the need for or a reduced need for sunlight. It is possible that chitosan activates a pathway or pathways necessary for both growth and lipid production without having to rely on chlorophyll and photosynthesis. Chitosan and/or chitin may be used to provide for the efficient growing of microalgae in optical fiber bioreactors having diffused light introduced into the bioreactor.

The disclosed method may also be used for the removal of microconstituents from water, such as dissolved substances that might include pharmaceuticals, endocrine disruptors, over-the-counter drugs, such as ibuprofen, aspirin, etc. The algae take up the microconstituents as it grows. The algae containing the microconstituents could then be removed from the water, such as employing one of the harvesting methods described herein. For example, the algae can be squeezed to remove the oil from the algae using a press. The pressed algae could be returned back to the water for continued growth and microconstituent removal or combusted to generate energy while simultaneously destroying the microconstituents contained within the algae. The pressed algae could be utilized as feedstock for ethanol production by fermentation. Algae growth under the conditions of fermentation could also be increased by the presence of chitosan and/or chitin.

Chitosan and/or chitin may provide an increase in the production of oxygen by algae. Chitosan and/or chitin may provide for enhanced oxidation of chemical substances taken up by algae. The increased generation of oxygen in the microalgae, as a result of growing in the presence of chitosan, would increase oxidation of the microconstituents contained therein. The algae could therefore act as biological decontamination units or water treatment units to clean up water that could be used for drinking, irrigation, or industrial uses. For example, the disclosed method may provide for reducing nutrients such as nitrogen and phosphorous in wastewater, or for reducing dissolved metals in water.

Chitosan and/or chitin may provide for an increase in astaxanthan production as compared to astaxanthan production achieved by growing microalgae in the absence of chitosan and/or chitin or chitosan and/or chitin and a polyanionic polymer, such as alginate or carrageenan.

Chitosan and/or chitin may increase the biomass of the microalgae for the purpose of using the microalgae for animal and fish feed, pigment extraction, vitamin production, as dietary supplements, ethanol production, specialty chemical production, antibiotic production, and/or energy generation through combustion or fermentation.

In the embodiments described above, chitosan and/or chitin, or other polycationic substances may be used alone or in any combination, and optionally with anionic substances.

DESCRIPTION OF THE DRAWINGS

The patent or application file contains at least one drawing executed in color. Copies of this patent or patent application publication with color drawing(s) will be provided by the Office upon request and payment of the necessary fee.

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1A:
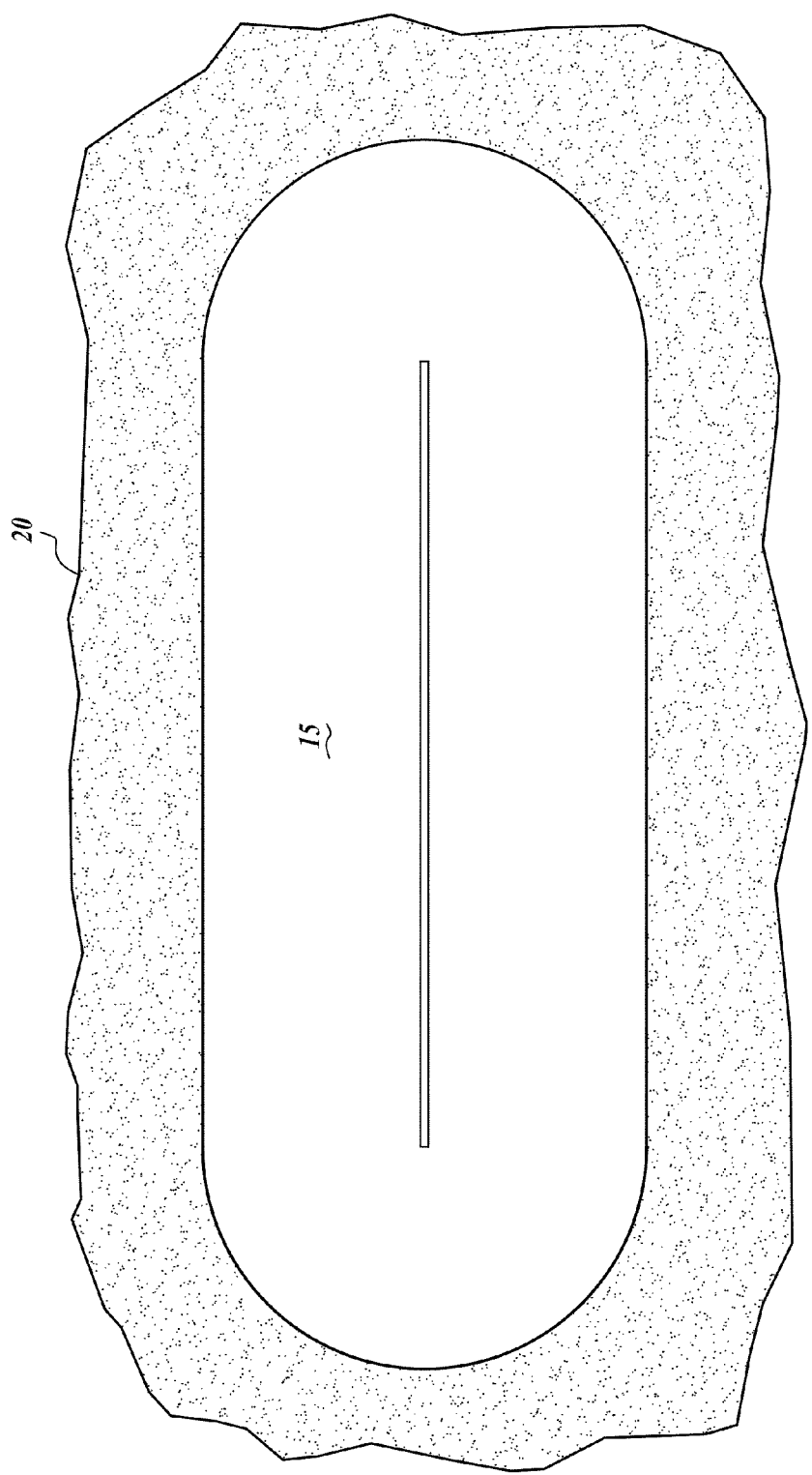
FIG. 1A is a diagrammatical illustration showing a plan view of a raceway pond.

This disclosure relates to a method of growing and harvesting algae by introducing an effective amount of chitosan and/or chitin to an environment suitable for growing algae, and cultivating the algae such that the chitosan increases the growth of the algae and causes the algae to grow into aggregated growths and/or mats. The chitosan and/or chitin may be soluble. Optionally, an anionic polysaccharide, such as alginate, carrageenan, pectin, anionic polyacrylamide, and xanthan gum, can be added. The method advantageously results in algae that can be harvested more readily when aggregated or grown as a mat. The algae can then be used as a source for biofuels, specialty chemicals, animal and fish feed, nutrients, ethanol production, biomass recovery useful for agriculture, and energy generation, such as methane combustion and ethanol production.

In a first embodiment, a method for growing algae is disclosed. The method includes, introducing an amount of chitosan to an aqueous environment suited for growing algae; cultivating algae in the environment in the presence of chitosan over a period of time; and increasing algae growth with chitosan in comparison to algae growth without chitosan.

In a second embodiment, a method for growing algae is disclosed. The method includes: introducing an amount of chitosan to an aqueous environment suited for growing algae; cultivating algae in the environment in the presence of chitosan over a period of time; and producing aggregated algae in the aqueous environment.

In a third embodiment, a method for increasing the lipid content of algae is disclosed. The method includes: introducing an amount of chitosan to an aqueous environment suited for growing algae; providing algae to the environment, wherein the algae has an initial lipid content per unit mass of algae; cultivating the algae in the environment in the presence of chitosan over a period of time; and increasing the lipid content per unit mass of algae grown with chitosan as compared to the initial lipid content of the algae.

In a fourth embodiment, a method for altering the lipid profile of algae is disclosed. The method includes, introducing an amount of chitosan to an aqueous environment suited for growing algae; providing algae to the environment, wherein the algae has an initial lipid profile comprising a plurality of lipid species; cultivating the algae in the environment in the presence of chitosan over a period of time; and altering the lipid profile of algae grown with chitosan as compared to the initial lipid profile of algae.

In a fifth embodiment, a method for removing constituents from water is disclosed. The method includes, introducing chitosan to an aqueous environment suited for growing algae, wherein the environment contains constituents desired to be removed; cultivating algae in the environment in the presence of chitosan over a period of time, wherein the constituents are taken up by the algae; and harvesting the algae to remove the constituents from the water.

The first through fifth embodiments may further include wherein algae growth is increased by at least 5% by weight as compared to algae growth without chitosan.

The first through fifth embodiments may further include wherein algae growth is increased by at least 10% by weight as compared to algae growth without chitosan.

The first through fifth embodiments may further include wherein algae growth is increased by at least 18% by weight as compared to algae growth without chitosan.

The first through fifth embodiments may further include wherein algae growth is increased by at least 400% by weight as compared to algae growth without chitosan.

The first through fifth embodiments may further include wherein the algae is a microalgae.

The first through fifth embodiments may further include wherein the algae growth is aggregated by the chitosan.

The first through fifth embodiments may further include wherein the algae is selected from at least one of a diatom, Green algae, Blue Green algae, Golden-brown algae, Prymnesiophyte or Eustigmatophyte.

The first through fifth embodiments may further include wherein the algae comprises lipids.

The first through fifth embodiments may further include further comprising draining the aqueous environment of water to harvest the algae.

The first through fifth embodiments may further include cultivating the algae in a porous containment device that is transportable within the aqueous environment.

The first through fifth embodiments may further include processing the algae into fuel.

The first through fifth embodiments may further include wherein the amount of chitosan is approximately 25 ppm to 100 ppm.

The first through fifth embodiments may further include wherein the amount of chitosan is approximately 150 ppm to 250 ppm.

The first through fifth embodiments may further include wherein the amount of chitosan is greater than 250 ppm.

The first through fifth embodiments may further include introducing a soluble anionic polymer to the aqueous environment.

The first through fifth embodiments may further include introducing at least one of alginate, carrageenan, xanthan gum, and anionic polyacrylamide to the environment.

The first through fifth embodiments may further include wherein the aqueous environment comprises a raceway pond having one or more holes on the bottom thereof to drain water.

The first through fifth embodiments may further include reducing or eliminating a source of light from the environment.

The first through fifth embodiments may further include reducing or eliminating a source of light from the environment without introduction of carbon-containing or protein-containing materials that cause the algae to grow.

The first through fifth embodiments may further include cultivating algae by at least one step selected from the group consisting of: introducing water to the aqueous environment, introducing nutrients to the aqueous environment, controlling the salinity of the aqueous environment, controlling the pH of the aqueous environment, and exposing the aqueous environment to a source of light.

The first through fifth embodiments may further include allowing time to grow the algae into one or a plurality of algae mats.

The first through fifth embodiments may further include harvesting aggregated algae.

The first through fifth embodiments may further include growing the algae into mats.

The first through fifth embodiments may further include assigning carbon credits to carbon dioxide consumed by the algae as a result of the increase in growth of the algae grown in the presence of chitosan. The amount of carbon dioxide used by an algae population grown in the absence of chitosan can be measured and compared to the amount of carbon dioxide used by an algae population grown in the presence of chitosan and the difference in carbon dioxide removed could be assigned a carbon credit value.

Referring to FIG. 1A, a diagrammatical illustration of an open conventional "raceway" pond 15 is provided. Raceway ponds are often employed in the cultivation of algae. A raceway pond 15 is illustrative of one embodiment of an environment suited for growing algae. Other environments commonly used for the growing of algae include tanks and circular ponds. While a method for growing algae is described in connection with an open raceway pond, other devices suitable for providing an environment for growing algae may be used, such as, but not limited to closed photosynthetic bioreactors. Raceway ponds are advantageous in that the ponds are simple to construct and operate. Raceway pond 15 can be built on surrounding land 20. Raceway ponds employed in the cultivation of algae may have means for the continuous circulation of water, algae, and nutrients around the raceway pond. A typical device used for circulation is a paddle wheel. Nutrients, including carbon dioxide and water, can be added to the raceway pond, while water containing the algae is removed. Raceway ponds are typically shallow to allow sunlight to penetrate throughout the depth of the pond. A detailed description of the construction and operation of a raceway pond is readily available from the literature. Disclosed herein is a method for growing and harvesting algae that includes the use of chitosan and/or chitin and optionally an anionic polymer during the growing of the algae.

As used herein, "algae" refers to microalgae. The algae for use in the disclosed method can include marine algae and freshwater algae. Algae for use in the disclosed method includes, but is not limited to: Diatoms (Class Bacillariophyceae); Green Algae (Class Chlorophyceae); Golden-Brown Algae (Class Chrysophyceae); Prymnesiophytes (Class Prymnesiophyceae), Eustigmatophytes (Class Eustigmatophyceae) and Blue Green Algae also referred to as Cyanobacteria (Class Cyanophyceae). Preferred algae for use in the disclosed method includes microalgae. Microalgae, as used herein, refers to single-celled photosynthetic microorganisms that utilize energy from sunlight, or otherwise, to combine water, nutrients, and carbon dioxide to produce biomass that can contain lipids. In the disclosed method, one or a plurality of species of algae may be simultaneously cultivated in an environment suited to the growth of the algae. The conditions suited for growth of a particular algae species can be determined from the literature. As disclosed herein, an effective amount of soluble chitosan and/or chitin may be added before or during the introduction of the algae to the environment. While any amount of chitosan may desirably result in increased growth and/or aggregated growths of algae, a chitosan range of approximately 25 ppm to 100 ppm and approximately 150 ppm to 250 ppm has been found to increase growth. Chitosan may also be added in any amount and then the growth rate can be determined gravimetrically to determine the optimal concentration of chitosan needed to achieve the highest growth yield for a particular algae. Chitosan may be added in any amount and then visual inspection may be used to determine whether the algae is aggregating or growing as mats. Upon determining visually that the algae is not aggregated, more chitosan may be added. Optionally, an anionic polysaccharide, such as alginate, pectin, carrageenan, and xanthan gum, may be added. The algae can then cultivated, such as, but not limited to the introduction of water, nutrients, carbon dioxide, exposure to sunlight or other light source that mimics sunlight, and subjected to pH control or salinity control. The chitosan and/or chitin may be used to grow the algae into aggregated growths or mats that make harvesting less complex. Further, the chitosan and/or chitin may be used to increase the rate of growth (by weight) of the algae as compared to the rate of growth of the algae in the absence of chitosan, all other conditions being equal. A further advantage may include higher lipid content in algae when grown in an environment containing chitosan and/or chitin.

In accordance with one embodiment, however, it is believed algae can be grown in the presence of chitosan by reducing or eliminating entirely sunlight or other light source. In the absence of light, chlorophyll production is greatly reduced with and without chitosan. Although the chlorophyll content of algae grown in the dark may be low, it is possible to grow a significant amount of algal biomass in the presence of chitosan. Grown in the dark and in the presence of chitosan, algae may grow as white, near-transparent algal growth without green pigments or chloroplasts. The growth of algae in the absence of photosynthesis is an indication that photosynthesis may have been decoupled, possibly driven by the presence of chitosan. The algae may have abandoned chlorophyll production in favor of chemotrophy.

Chitin is a polymer that occurs widely in nature and is a principal constituent of the exoskeleton of many arthropods and insects, and of the cell wall of many fungi. It is frequently found in a mixture with proteins and calcium compounds. Chitin is essentially a polymer of 2-deoxy-2-acetamidoglucose monomer units that are linked in beta-1,4 fashion though a minor fraction of the units may be hydrolyzed to 2-deoxy-2-aminoglucose units. The term chitosan is generally applied to copolymers having greater than 50% 2-deoxy-2-aminoglucose monomeric units and the remaining monomeric units being 2-deoxy-2-acetamidoglucose units. Chitosan is derived from chitin by hydrolysis of some 2-deoxy-2-acetamidoglucose units to 2-deoxy-2-aminoglucose units. Due to the presence of a greater number of free amino groups, chitosan is soluble in aqueous acidic solutions and is present in such media as a polycation with the protonated amino group bearing a positive charge. Chitosan useful in the method disclosed herein typically has a molecular weight in the range of from 20,000 Daltons to two million Daltons, such as from 50,000 Daltons to one million Daltons, or such as from 100,000 Daltons to 900,000 Daltons. Chitosan useful in the disclosed methods typically has a percentage deacetylation of from 50% to 100%, such as from 60% to 95%, or from 70% to 90%. Chitosan for use in the disclosed methods may be provided as a salt of chitosan with a $C_1$ to $C_{18}$ mono- or polycarboxylic acid, such as chitosan acetate or chitosan lactate. By way of non-limiting example, chitosan salts useful in the practice of the invention include: chitosan glutamate, chitosan hydrochloride, chitosan succinate, chitosan fumarate, chitosan adipate, chitosan glycolate, chitosan tartrate, chitosan formate, chitosan malate, chitosan lactate, chitosan pyruvate, and chitosan citrate.

Chitosan, provided either in solution or as a solid, can be introduced continuously or intermittently into an environment suited for growing algae. The effective concentration, based on a weight percent of chitosan to the aqueous media in which the algae is growing, is believed to be in the range of approximately 25 ppm to 100 ppm and approximately 150 ppm to 250 ppm. Although any amount of chitosan may show desirable effects on the algae. It is believed that chitosan can provide one or more advantages when used in the growing and cultivation of algae. Chitosan can cause the microalgae to grow as an aggregated growth or mat that is stable to dissociation and allows the harvesting of algae with less complex devices than what is currently used. Chitosan can cause an increase in the growth rate of the algae, as compared to algae that is not treated with chitosan, resulting in a greater amount of biomass accumulation over an equal period of time. One experimental test resulted in an increase of approximately 18% by weight. Another experimental test resulted in an increase of approximately 412% by weight (see Example 5 below). Accordingly, an increase of 5% by weight, 10% by weight, 18% by weight, 400% by weight, and greater may be achievable in full scale commercial ponds. Chitosan may cause an increase in the quantity of lipids produced by algae. Accordingly, higher lipid yields may be realized. Chitosan may alter the lipid profile of the algae grown with chitosan. Chitosan may cause an increase in the synthesis of the enzyme Acetyl CoA Carboxylase in algae. Chitosan may increase the utilization of carbon dioxide by microalgae. Chitosan may influence the photosynthetic pigments, such as chlorophyll and/or carotenoid pigments content and/or their ratios.

Other polycationic substances besides chitosan and chitin could exhibit the same effects on microalgae growth and lipid yield and/or produce similar aggregated or mat growth structures. Other representative polycationic substances include, but are not limited to: polycationic acrylamide; cationic guar; cationic starch; certain polyamines and other natural or synthetic cationic polymers. Additionally, the method disclosed herein also comprises growing algae in the presence of chitosan in combination with xanthans or other anionic polysaccharides, such as alginate, carrageenan, pectin, and carboxymethylcellulose.

Representative growing environments will now be described that facilitate the harvesting of algae grown in the presence of chitosan. It is to be understood that other environments may be used besides the open raceway ponds specifically mentioned below.

The disclosure of representative environments should not be construed to limit the invention to any one particular embodiment.

Figure 1B:
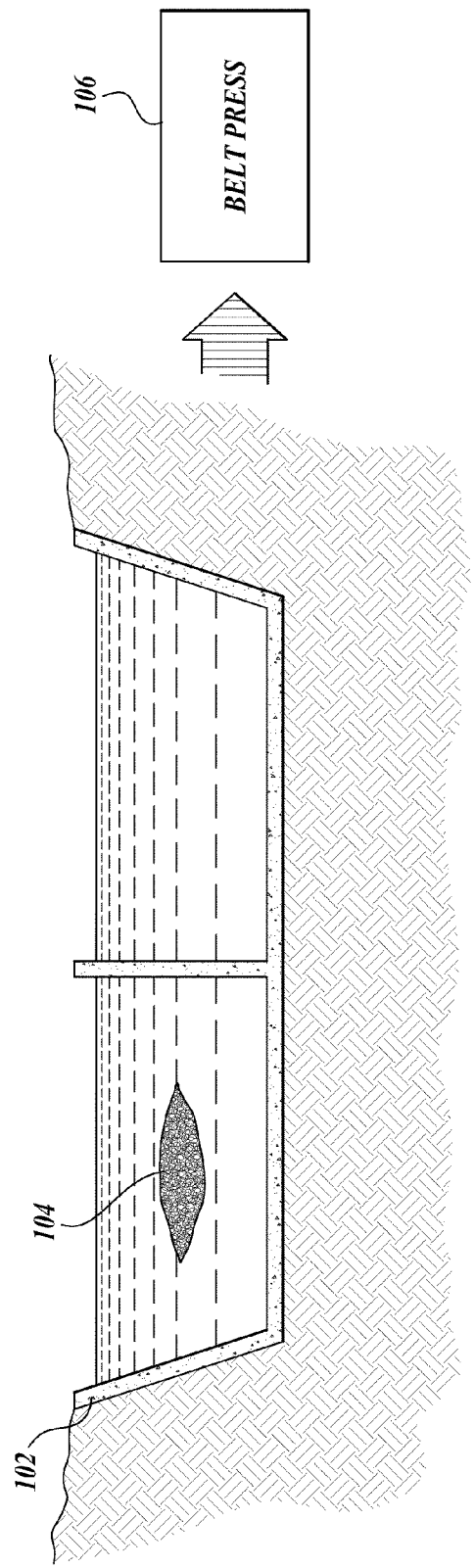
FIG. 1B is a diagrammatical illustration showing a cross sectional view of a raceway pond according to one embodiment of the invention.

Referring to FIG. 1B, a cross sectional view of a raceway pond 102 in accordance with one embodiment of the present invention is illustrated. In the disclosed embodiment, a containment device 104 is provided in which the algae is permitted to grow. As disclosed above, the cultivation of algae may include the introduction of water, nutrients, carbon dioxide, exposure to sunlight or other light source that mimics sunlight, and subjected to pH control or salinity control. To the raceway pond 102, there is also added an effective amount of chitosan or chitin or both, and, optionally, one or more anionic polymers. The containment device 104 is made from porous synthetic and/or non-synthetic woven or nonwoven fabrics. The chitosan-aggregated or chitosan-anionic polymer aggregated algae can be grown in a plurality of porous containment devices 104, which are placed within the raceway pond 102. The porous fabrics allow the nutrients to pass through and permit the algae to grow inside the containment device(s) 104. However, the chitosan-aggregated or chitosan-xanthan aggregated algae are stable to dissociation and are larger than what the porous fabric allows to pass through. The containment device 104 can make harvesting easier by simply removing the containment device 104 containing the aggregated/clumped/mat of algae from the water and pressing to a paste-like consistency using a belt press 106, or other suitable dewatering device. The containment device 104 allows liquids, nutrients, oxygen, and sunlight to pass through the porous fabrics of the containment device 104. The porous containment device 104 containing the aggregated algae can be transported throughout the aqueous medium to bring the algae closer to a source of light energy such as the sun. Alternatively, the containment device 104 can be moved away from the source of light energy in order to provide diffuse light and protect the algae from the intensity of the light energy. To harvest the algae, the containment device 104 may be placed on a belt press. The press squeezes the water from the inside of the containment device 104, separating the water from the algae. Thereafter, the containment device 104 can be opened to collect the microalgae.

Figure 1C:
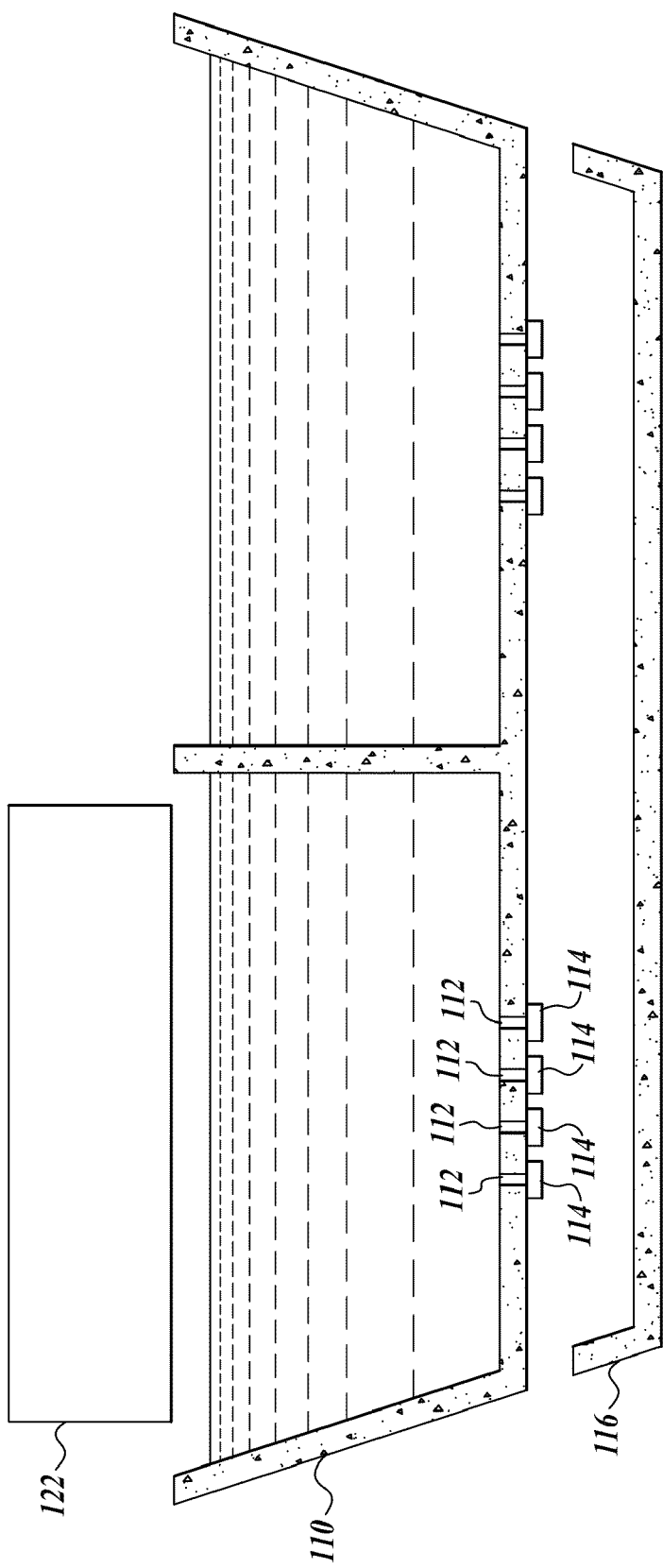
FIG. 1C is a diagrammatical illustration showing a cross sectional view of a raceway pond according to one embodiment of the invention.

Another embodiment of the invention comprises growing the chitosan-aggregated or chitosan-anionic polymer aggregated algae in a raceway pond containing blocked holes throughout the bottom of the raceway. As illustrated in FIG. 1C, a raceway pond 110 is provided with holes 112 throughout the bottom of the raceway pond 110. Each individual hole 112 may be blocked by a sliding plate 114. Alternatively, a large plate may block a multiplicity of the holes 112. Beneath the raceway pond 110, a containment pond 116 is provided underneath the holes 112 to catch the water when draining the raceway pond 110. The raceway pond 110 may be operated batchwise including periods for growing the algae and periods for harvesting the algae. During the growing period, the holes 112 remain blocked. As disclosed above, the cultivation of algae may include the introduction of water, nutrients, carbon dioxide, exposure to sunlight or other light source that mimics sunlight, and subjected to pH control or salinity control. To the raceway pond 110, there is also added an effective amount of chitosan or chitin or both, and optionally, xanthan gum. During the growing period, the algae grows as aggregated growths or mat structures that are stable to dissociation. Harvesting the chitosan-aggregated or chitosan-xanthan aggregated algae that have settled on the raceway bottom can be accomplished by opening the covered holes 112 by sliding the plates 114 in one direction and allowing the water to drain into the containment pond 116 positioned below the raceway pond 110. The holes 112 are sized large enough such that the chitosan-aggregated or chitosan-xanthan aggregated algae are larger than the holes and avoid passing through the holes 112 and will remain in the raceway pond 110 after draining. When the raceway pond 110 is emptied of water, the algae remains on the bottom surface of the raceway pond 110. The aggregated algae in the drained raceway pond 110 can then be collected from the raceway pond 110 using a moving scraper or spatula device 122 configured to fit the contour of the raceway pond bottom. The collected water in the containment pond 116 can be pumped back into the raceway pond 110 after the holes 112 are closed by sliding the plates 114 back in place, and a new batch of algae may be cultivated.

Figure 1D:
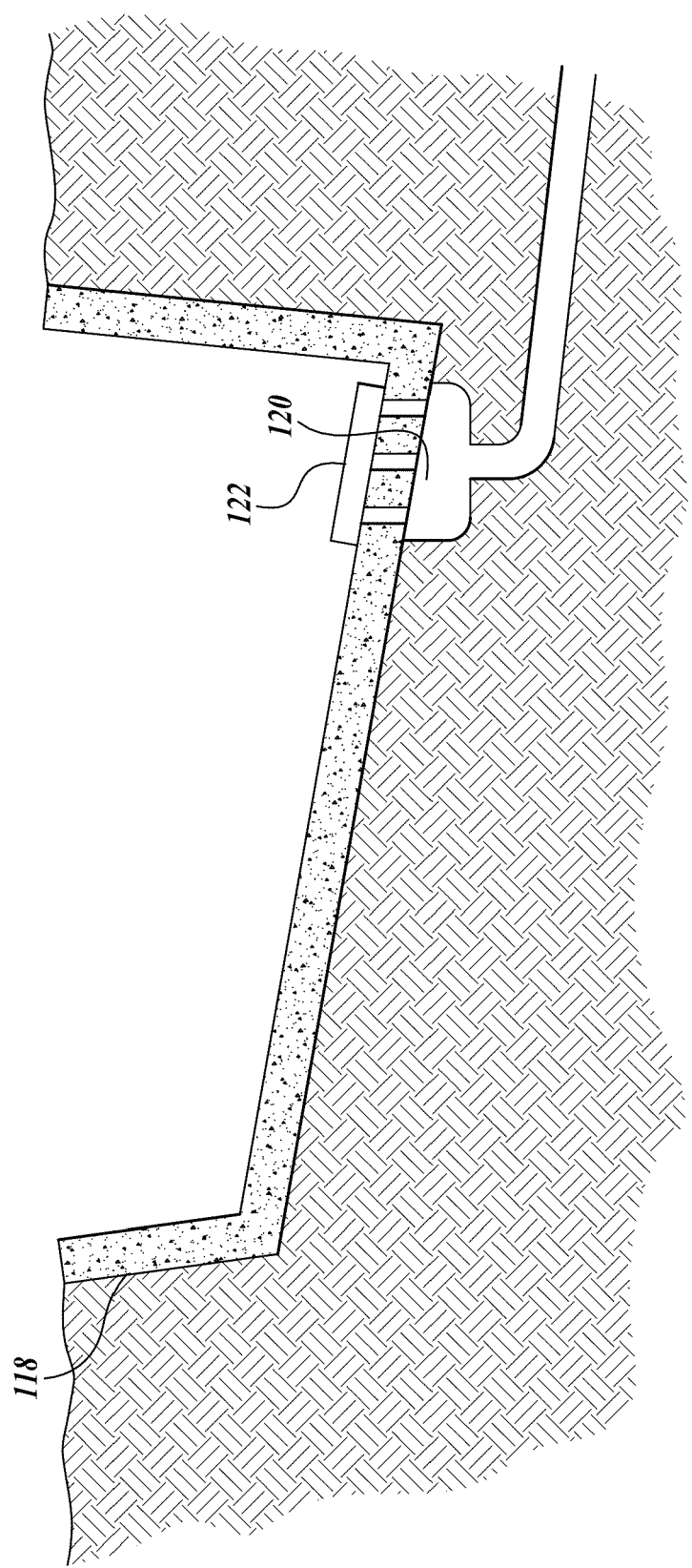
FIG. 1D is a diagrammatical illustration showing a cross sectional view of a raceway pond according to one embodiment of the invention.

Another embodiment of the invention comprises growing the chitosan-aggregated or chitosan-xanthan aggregated algae in a sloped raceway pond with a drain. As illustrated in FIG. 1D, one end of the raceway pond 118 is elevated in relation to the opposite end to provide a slope throughout the length of the raceway pond 118. The end that is lower in elevation is provided with a drain 120. A plate 122 blocks the drain 120 which is closed during the growing cycle of the algae. As disclosed above, the cultivation of algae may include the introduction of water, nutrients, carbon dioxide, exposure to sunlight or other light source that mimics sunlight, and subjected to pH control or salinity control. To the raceway pond 118, there is also added an effective amount of chitosan or chitin or both, and, optionally, xanthan gum.

During the growing period, the algae grows as aggregated growths or mat structures stable to dissociation. To empty the raceway pond 118 of water, the plate 122 is slid to the side, thus allowing the water to drain out of the raceway pond 118. The drain holes 120 are small enough such that chitosan-aggregated or chitosan-xanthan aggregated algae will remain on the bottom surface of the raceway pond 118 and not pass through the drain holes 120. Similar to the embodiment illustrated in FIG. 1C, the aggregated algae in the drained raceway pond 118 can then be collected from the raceway pond 118 using a moving scraper or spatula device configured to fit the contour of the raceway pond bottom.

While illustrative embodiments have been illustrated and described, it will be appreciated that various changes can be made therein without departing from the spirit and scope of the invention. For example, the algae can be grown, in the presence of chitosan and/or chitin and optionally xanthan, in any raceway pond or tank and the algae harvested by conventional means, such as disclosed in the background section of this disclosure.

EXAMPLES

Example 1

Growing Aggregated Algae with Chitosan

Figure 2:
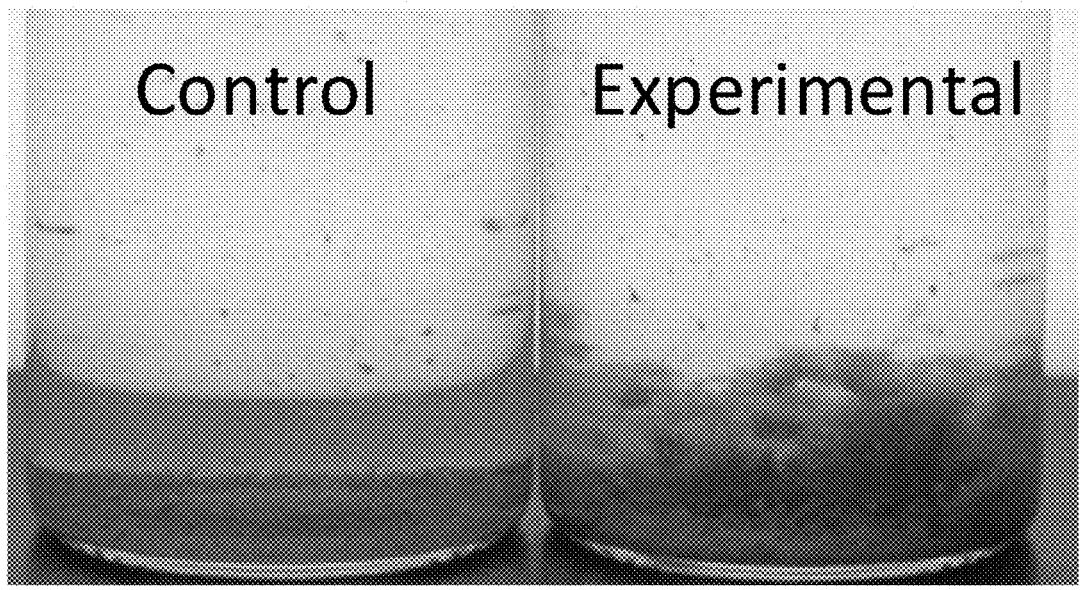
FIG. 2 is a photograph a sample of aggregated microalgae treated with chitosan (Experimental) and an untreated sample of microalgae (Control)

An equal suspension of freshwater Green microalgae was added to two containers of water containing equal concentrations of macronutrients and micronutrients shown below in Tables 11 and 12, wherein 10 ml of each nutrient were added per liter of water instead of 4 ml. Chitosan acetate solution (1% by weight chitosan, 1% by weight glacial acetic acid, 98% by weight water) was added to the container labeled "experimental" to reach a concentration of 150 ppm by weight chitosan that is sufficient to cause flocculation of the microalgae. The container labeled "control" received no chitosan. After one week, the sample that had been treated with chitosan exhibited significantly more growth in the form of a large aggregated clump-like mass compared to the control, which exhibited growth as a thin layer on the bottom of container as shown in FIG. 2. When disturbed by agitating the containers equally, the microalgae grown in the aggregated clump-like mass in the experimental container stayed together compared to the microalgae in the control container that tended to disperse throughout the water.

Example 2

Growing Algae into Mats with Chitosan

Figure 3:
FIG. 3 is a photograph of a sample of microalgae treated with chitosan that has grown as into a mat structure.

Freshwater Green microalgae were made to grow in a mat-like structure by adding chitosan acetate solution (1% by weight chitosan acetate, 1% by weight glacial acetic acid, 98% by weight water) to reach a concentration of approximately 130-150 ppm by weight of chitosan in a growing suspension of microalgae. Microalgae growing in the presence of chitosan initially formed flocs and loose aggregates following the addition of chitosan. In approximately 4 weeks, while continuing to grow in the presence of chitosan, the algae grew in the form of an aggregated mat resembling turf as seen in FIG. 3.

Example 3

Increasing the Algae Growth Rate with Chitosan

Figure 4:
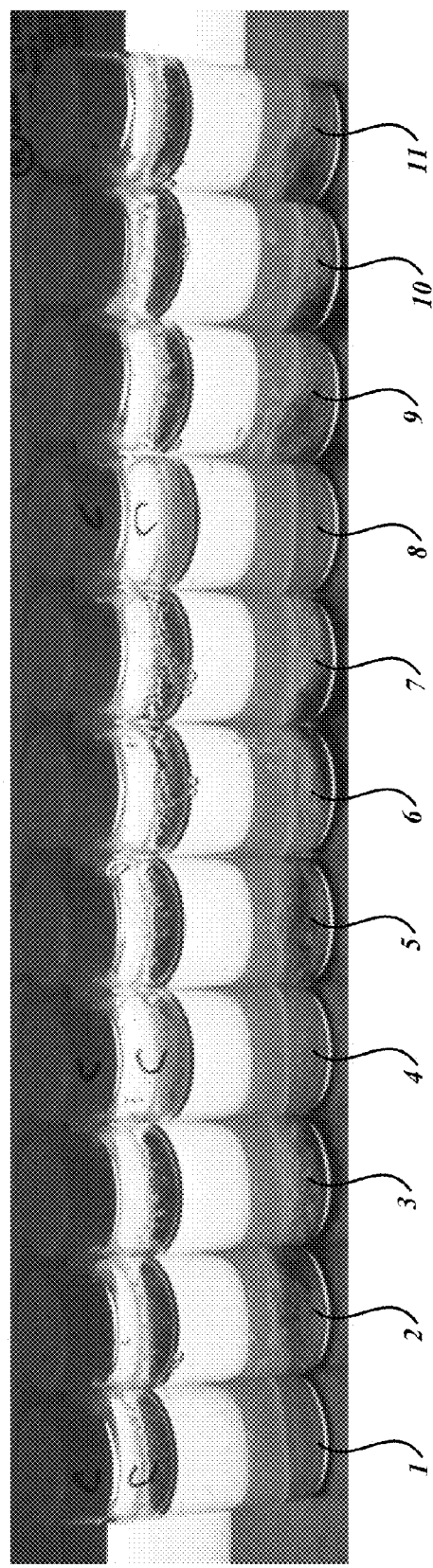
FIG. 4 is a photograph of samples of microalgae treated with chitosan (unmarked) and untreated samples (C), wherein the treated samples show greater bubble generation.

Test 1: Diluted stock Green microalgae solution was used for the sample in this test. Since the algae was diluted, its growth and structure could be monitored over time. Two bottles of diluted algae sample were made. A chitosan acetate solution (1% by weight chitosan acetate, 1% by weight glacial acetic acid, 98% by weight water) was added to one of the bottles (experimental) to reach a concentration of 150 ppm by weight of chitosan. The other bottle served as the control, and contained no chitosan. An equal amount of fertilizer comprising the nutrients as described in Example 1 was added to both the control and experimental bottles as a nutrient source. Five 20 ml samples were removed from the control, and ten 20 ml samples were removed from the experimental. All the samples were placed on the window sill. As the algae grew, the difference between the chitosan treated and control sample with no chitosan could be seen. The experimental sample with chitosan had large clumps of algae growth on the bottom of the vial. The control with no chitosan had flat growth on the bottom of the vial. After 14 days the vials were examined. As seen in FIG. 4, the vials with a "C" are the control vials with no chitosan, whereas the unmarked vials are the experimental and have been treated with chitosan. As was observed in Example 1, the chitosan treated samples had large aggregated microalgae growth and the control samples did not. The samples were then vigorously mixed in order to sufficiently disperse the microalgae. The absorbance of light energy at 600 nm for each sample was then measured using a UV-Vis spectrophotometer. The results are shown below in Table 1. It is presumed that the greater the absorbance the more algae is present. The average absorbance for the control was 1.159 versus the experimental of 1.441 showing that the chitosan treated samples had more growth as measured by absorbance at 600 nm. It was also observed that aggregated clumped microalgae growing in the presence of soluble chitosan generated more bubbles of oxygen compared to microalgae controls that contained no chitosan. The gas bubbles at the surface of the water in the experimental vials containing microalgae and chitosan can be clearly seen in FIG. 4 by comparing experimental vials numbered 2, 6, 7, 9, and 10 with control vials numbered 1, 4, and 8.

TABLE 1

| Sample Absorbance | | | |
|---|---|---|---|
| Sample | ABS 600 nm | Sample | ABS 600 nm |
| C1 | 1.036 | E1 | 1.443 |
| C2 | 1.198 | E2 | 1.310 |
| C3 | 1.192 | E3 | 1.465 |
| C4 | 1.211 | E4 | 1.382 |
| C5 | 1.160 | E5 | 1.428 |
|  |  | E6 | 1.515 |
|  |  | E7 | 1.499 |
|  |  | E8 | 1.401 |
|  |  | E9 | 1.502 |
|  |  | E10 | 1.465 |
| Ave | 1.159 | Ave | 1.441 |

Since the above test did not use up all of the test sample, what was left was further processed to collect more data. The samples were dried to remove the water, and the dried algae weighed to determine the difference in algae weight between the sample sets. It is presumed the greater the weight, the greater the algae growth. The weight data is shown below in Table 2. The final number to review is the ratio of the weight of dried algae per amount of sample dried. This calculation had to be performed because the amount of sample to be dried varied somewhat between samples. The difference between the control and the experimental was a 17.8% increase in the weight (growth) of the chitosan treated sample versus the control that was not treated with chitosan.

TABLE 2

Chitosan Concentration vs. Algae Weight

| Sample | Pan Tare | Sample Wt/Pan | Sample Wt | Dry Wt/Pan | Dry Wt | Ratio AL per gm |
|---|---|---|---|---|---|---|
| C1 | 1.4204 | 14.7355 | 13.3151 | 1.4306 | 0.0102 | 0.000766 |
| C2 | 1.4151 | 13.616 | 12.2009 | 1.4239 | 0.0088 | 0.000721 |
| C3 | 1.4325 | 15.4516 | 14.0191 | 1.4424 | 0.0099 | 0.000706 |
| C4 | 1.4288 | 14.1363 | 12.7075 | 1.4394 | 0.0106 | 0.000834 |
| C5 | 1.4246 | 14.24 | 12.8154 | 1.4368 | 0.0122 | 0.000952 |
|  |  |  |  |  | average | 0.000796 |
| E1 | 1.4257 | 15.1762 | 13.7505 | 1.4387 | 0.013 | 0.000945 |
| E2 | 1.4279 | 15.9331 | 14.5052 | 1.4408 | 0.0129 | 0.000889 |
| E3 | 1.4158 | 15.4057 | 13.9899 | 1.4284 | 0.0126 | 0.000901 |
| E4 | 1.4275 | 15.2293 | 13.8018 | 1.4394 | 0.0119 | 0.000862 |
| E5 | 1.4337 | 15.1678 | 13.7341 | 1.4464 | 0.0127 | 0.000925 |
| E6 | 1.4374 | 14.7913 | 13.3539 | 1.4504 | 0.013 | 0.000973 |
| E7 | 1.4275 | 14.7555 | 13.328 | 1.4405 | 0.013 | 0.000975 |
| E8 | 1.423 | 14.8115 | 13.3885 | 1.4351 | 0.0121 | 0.000904 |
| E9 | 1.4206 | 15.7854 | 14.3648 | 1.4345 | 0.0139 | 0.000968 |
| E10 | 1.428 | 15.2681 | 13.8401 | 1.4423 | 0.0143 | 0.001033 |
|  |  |  |  |  | average | 0.000938 |

E-C 0.000142
% growth gain 17.8%

Test 2: A dose response experiment was performed to determine the growth response of the algae to different concentrations of chitosan. The concentrations (by weight) of chitosan used and the results are shown below in Tables 3 and 4 as well as FIGS. 5 and 6. As before, the absorbance of each sample was measured to determine the concentration of algae and then the sample was dried to determine the weight of algae in the sample.

TABLE 3

Chitosan Concentration vs. Absorbance

| Sample | Chitosan ppm | ABS 600 nm |
|---|---|---|
| C | 0 | 1.240 |
| 1 | 10 | 1.205 |
| 2 | 20 | 1.334 |
| 3 | 30 | 1.258 |
| 4 | 40 | 1.278 |
| 5 | 50 | 1.335 |
| 6 | 60 | 1.329 |
| 7 | 70 | 1.368 |
| 8 | 80 | 1.345 |
| 9 | 90 | 1.375 |
| 10 | 100 | 1.320 |
| 11 | 125 | 1.260 |
| 12 | 150 | 1.300 |
| 13 | 175 | 1.375 |
| 14 | 200 | 1.202 |
| 15 | 225 | 1.226 |
| 16 | 250 | 1.149 |
| 17 | 1 | 1.086 |
| 18 | 5 | 1.060 |

TABLE 4

Chitosan Concentration vs. Sample Weight

| Sample | Pan Tare | Sample Wt/Pan | Sample Wt | Dry Wt/Pan | Dry Wt | Ratio AL per gm |
|---|---|---|---|---|---|---|
| C | 1.4285 | 20.7294 | 19.3009 | 1.4447 | 0.0162 | 0.000839 |
| 1 | 1.4145 | 21.6513 | 20.2368 | 1.4314 | 0.0169 | 0.000835 |
| 2 | 1.4231 | 21.608 | 20.1849 | 1.4399 | 0.0168 | 0.000832 |
| 3 | 1.4150 | 22.0223 | 20.6073 | 1.4319 | 0.0169 | 0.00082 |
| 4 | 1.4254 | 21.4948 | 20.0694 | 1.4421 | 0.0167 | 0.000832 |
| 5 | 1.4235 | 21.4642 | 20.0407 | 1.4412 | 0.0177 | 0.000883 |
| 6 | 1.4394 | 21.6186 | 20.1792 | 1.4580 | 0.0186 | 0.000922 |
| 7 | 1.4215 | 21.2654 | 19.8439 | 1.4404 | 0.0189 | 0.000952 |
| 8 | 1.4157 | 22.4181 | 21.0024 | 1.4361 | 0.0204 | 0.000971 |
| 9 | 1.4032 | 20.9755 | 19.5723 | 1.4237 | 0.0205 | 0.001047 |
| 10 | 1.4216 | 21.7168 | 20.2952 | 1.4399 | 0.0183 | 0.000902 |
| 11 | 1.4261 | 21.4119 | 19.9858 | 1.4424 | 0.0163 | 0.000816 |
| 12 | 1.4337 | 21.22 | 19.7863 | 1.4513 | 0.0176 | 0.00089 |
| 13 | 1.4169 | 21.3285 | 19.9116 | 1.4368 | 0.0199 | 0.000999 |
| 14 | 1.4305 | 20.7626 | 19.3321 | 1.4499 | 0.0194 | 0.001004 |
| 15 | 1.4301 | 21.5639 | 20.133 | 1.4502 | 0.0201 | 0.000998 |
| 16 | 1.4349 | 21.4895 | 20.0546 | 1.4555 | 0.0206 | 0.001027 |
| 17 | 1.4239 | 20.8876 | 19.4637 | 1.4386 | 0.0147 | 0.000755 |
| 18 | 1.4279 | 21.2496 | 19.8217 | 1.4440 | 0.0161 | 0.000812 |

Figure 5:
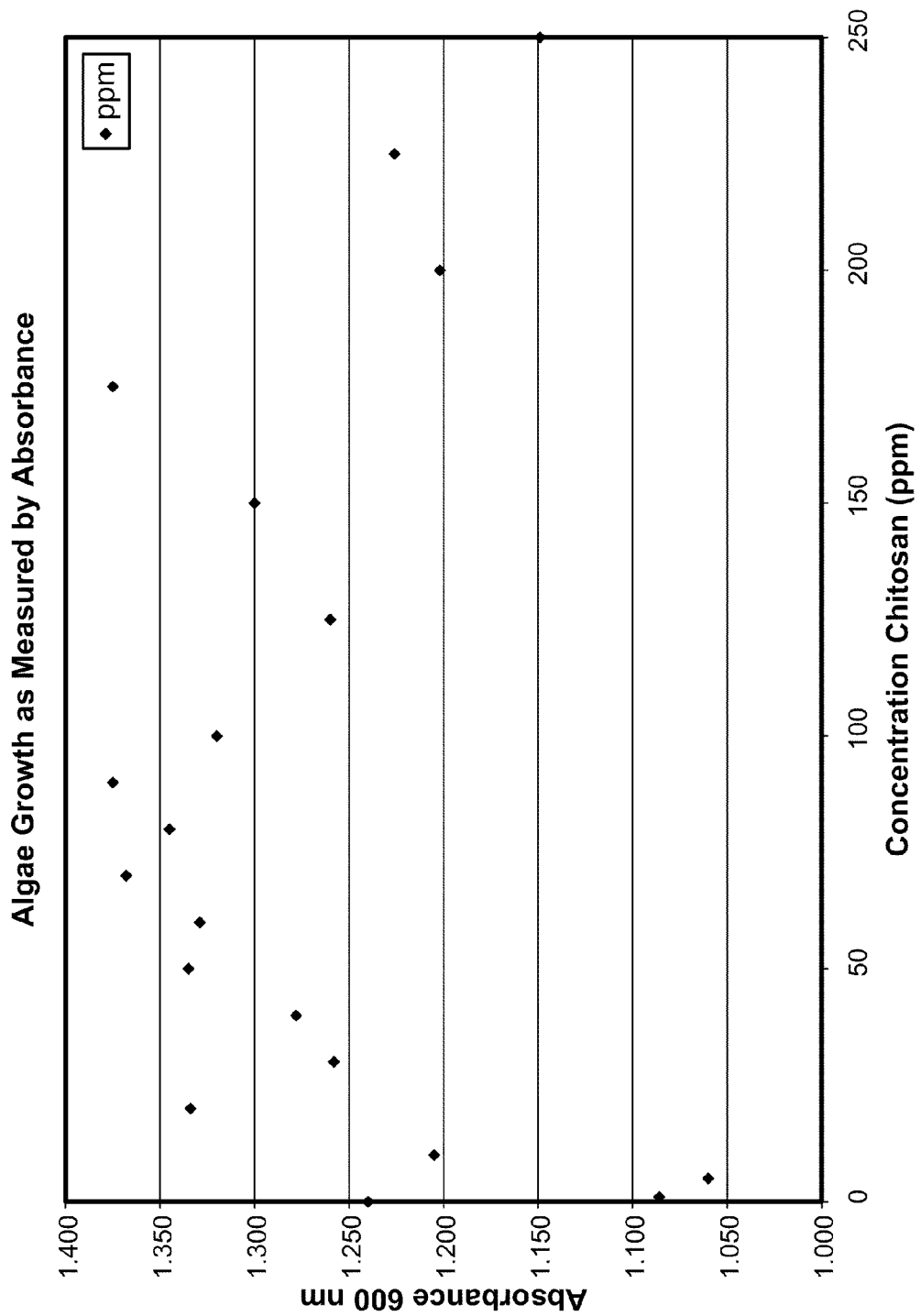
FIG. 5 is a graph showing the relationship of chitosan concentration to algae growth as measured by absorbance.
Figure 6:
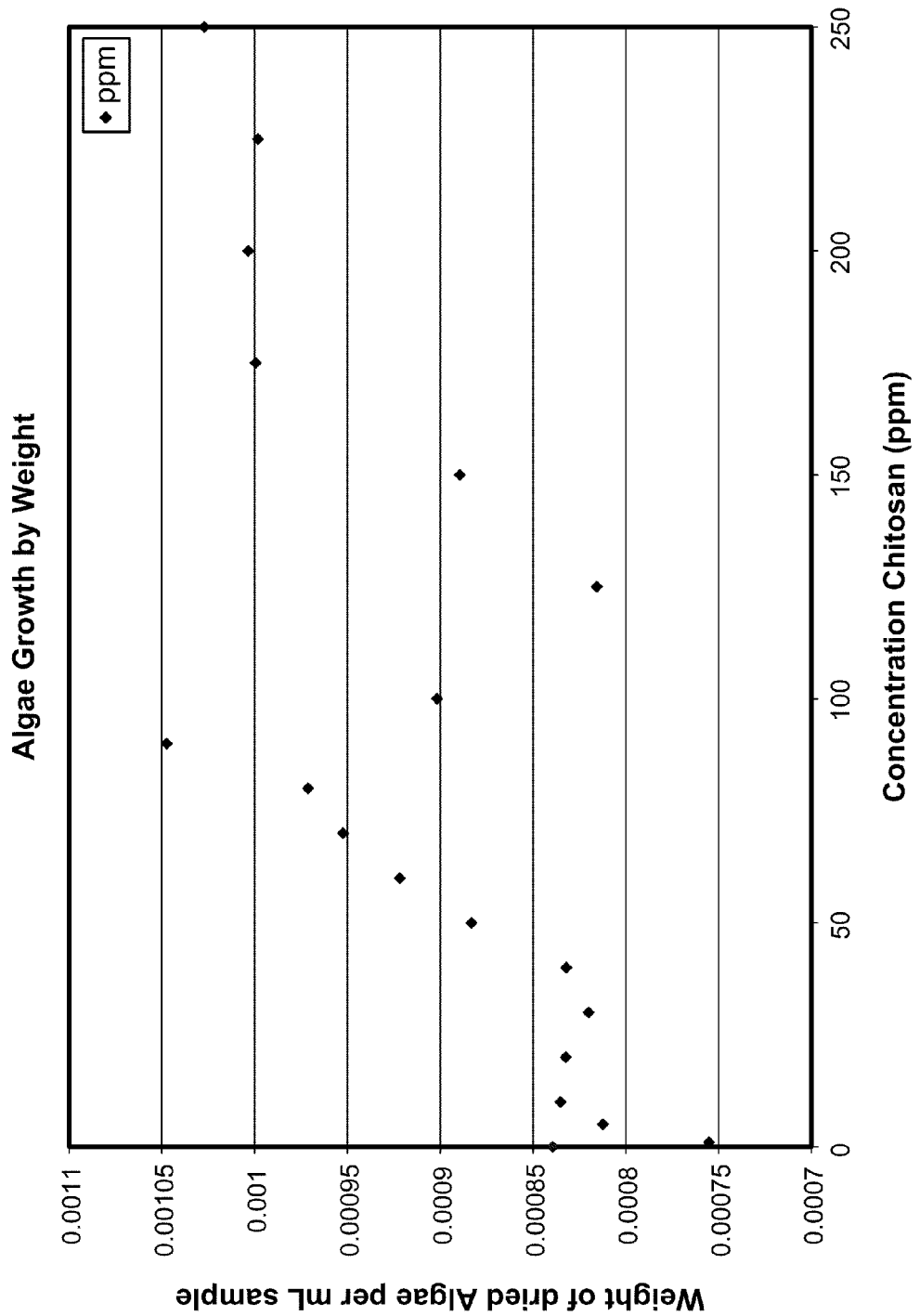
FIG. 6 is a graph showing the relationship of chitosan concentration to algae growth by weight.
Figure 7:
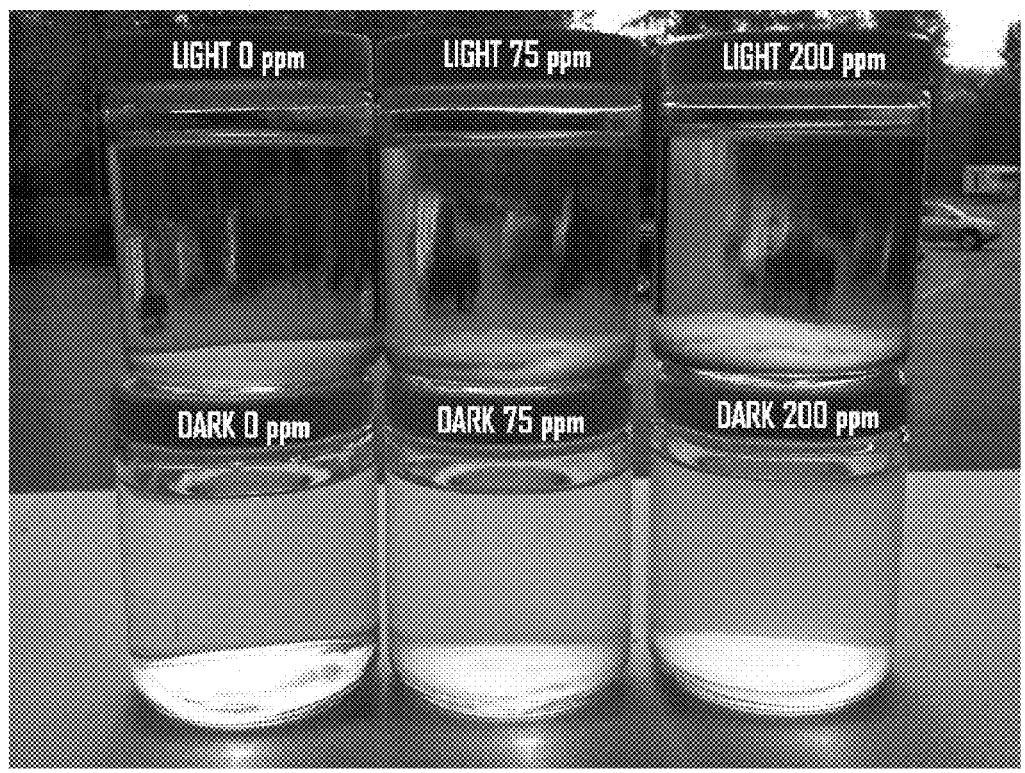
FIG. 7 is a photograph of samples of microalgae grown under dark and light conditions with varying amounts of chitosan.

As seen in FIG. 6, the bimodal nature of the growth response curve suggests a dose-dependent effect of chitosan on microalgae growth. Increased growth is observed from approximately 25 ppm up to 100 ppm and again at greater than 150 ppm chitosan. Interestingly, growth was inhibited between 100 ppm up to 150 ppm chitosan. The data presented in FIG. 6 demonstrate that algae growth is influenced by the concentration of chitosan in solution and can be enhanced to different degrees depending on the concentration of chitosan. The increased biomass observed from 175 ppm-250 ppm chitosan as seen in FIG. 6 exhibits lower absorbance at 600 nm (as seen in FIG. 5) as compared to the higher absorbance measured at 600 nm that corresponds to the lower biomass observed between 100-150 ppm chitosan (FIG. 6). The microalgae growing at concentrations of approximately 175 ppm-250 ppm chitosan exhibited a much lighter green color compared to the microalgae growing in chitosan concentrations approximately less than 150 ppm. This suggests that the increased biomass attributed to higher chitosan concentrations is not completely dependent on the chlorophyll content of the microalgae. It is likely that the dependence of microalgae on photosynthesis for growth can be overcome by the presence of a cationic polymer such as chitosan. Other cationic substances may produce the same effect as chitosan, such as polycationic species and small molecule cationic species. Greatest increase in algae growth can be observed in the range of 80 to 90 ppm, which shows an increase of approximately 20% by weight.

Example 4

Algae Grown with Chitosan in the Absence of Light

Procedure

Freshwater Green algae was used to inoculate 3 L of a freshly prepared growth medium. The diluted algae solution was then placed on the laboratory window sill for one week to allow for actively growing stock suspension. This algae culture was used to prepare all of the samples in this example.

After one week, the actively growing algae stock suspension was vigorously shaken, followed by mixing with a stir bar for 5 minutes to ensure a homogeneous algae suspension. The algae suspension was then filtered through a piece of fine plastic mesh to remove any large chunks, thereby creating a uniform and homogeneous algae growth suspension with which to inoculate all treatment solutions.

Next, 3.6 L of DI water were spiked with 4 mL of a stock macronutrient concentrate and 4 mL of a stock micronutrient concentrate found in Table 5 & 6.

TABLE 5

Macronutrients (Adjusted to pH-7.5)

| Macronutrient | Concentrate (g/L) | Target in Final Solution (mg/L) |
|---|---|---|
| $CaCl_2*2H_2O$ | 4.41 | 4.41 |
| $K_2HPO_4$ | 1.044 | 1.044 |
| $MgCl_2$ | 5.7 | 5.7 |
| $MgSO_4*7H_2O$ | 14.7 | 14.7 |
| $NaHCO_3$ | 15 | 30* |
| $NaNO_3$ | 1.044 | 1.044 |

TABLE 6

Micronutrients (Adjusted to pH-7.5)

| Micronutrient | Concentrate (g/L) | Target in Final Solution (mg/L) |
|---|---|---|
| $CoCl_2*2H_2O$ | 0.001428 | 0.001428 |
| $CuCl_2*2H_2O$ | 0.000012 | 0.000012 |
| $FeCl_3*6H_2O$ | 0.16 | 0.16 |
| $H_3BO_3$ | 0.1855 | 0.1855 |
| $MnCl_2*4H_2O$ | 0.4154 | 0.4154 |
| $Na_2EDTA*2H_2O$ | 0.3 | 0.3 |
| $Na_2MoO_4*2H_2O$ | 0.00726 | 0.00726 |

*Additional $NaHCO_3$ was added to the final solution to raise the total-$HCO_3$ concentration.

400 mL of the filtered homogeneous algae suspension was added to the DI-growth solution.

A total of 18-200 mL glass jars and lids were hand washed with detergent, rinsed, and dried. Each jar was filled with 200 g of the fresh algae suspension. 1.5 mL of a 1% (wt./wt.) chitosan acetate solution was added to each of 6 jars to create a 75 ppm chitosan concentration, and 4 mL of the 1% (wt./wt.) chitosan acetate solution was added to each of 6 jars to create a 200 ppm chitosan concentration. The remaining 6 jars did not receive any chitosan acetate solution and served as 0 ppm chitosan controls.

A large cardboard shipping box was lined with aluminum foil so no light could penetrate, and 9 total jars (3 jars of the 0 ppm control, 3 jars of the 75 ppm chitosan and 3 jars of the 200 ppm chitosan) were placed inside the box. The aluminum foil was then securely fitted around the tops of the jars so no light would penetrate the overlapping edges of foil. The box was then closed, sealed with tape, and placed on the laboratory window sill. To avoid pulses of light that could influence growth, the box would remain sealed until all samples were ready to be harvested.

The 9 remaining algae samples (3 jars of the 0 ppm control, 3 jars of the 75 ppm chitosan and 3 jars of the 200 ppm chitosan) were placed next to the sealed box on the window sill exposed to daylight. All samples would remain undisturbed on the window sill for a total of 10 days.

Results

Figure 8:
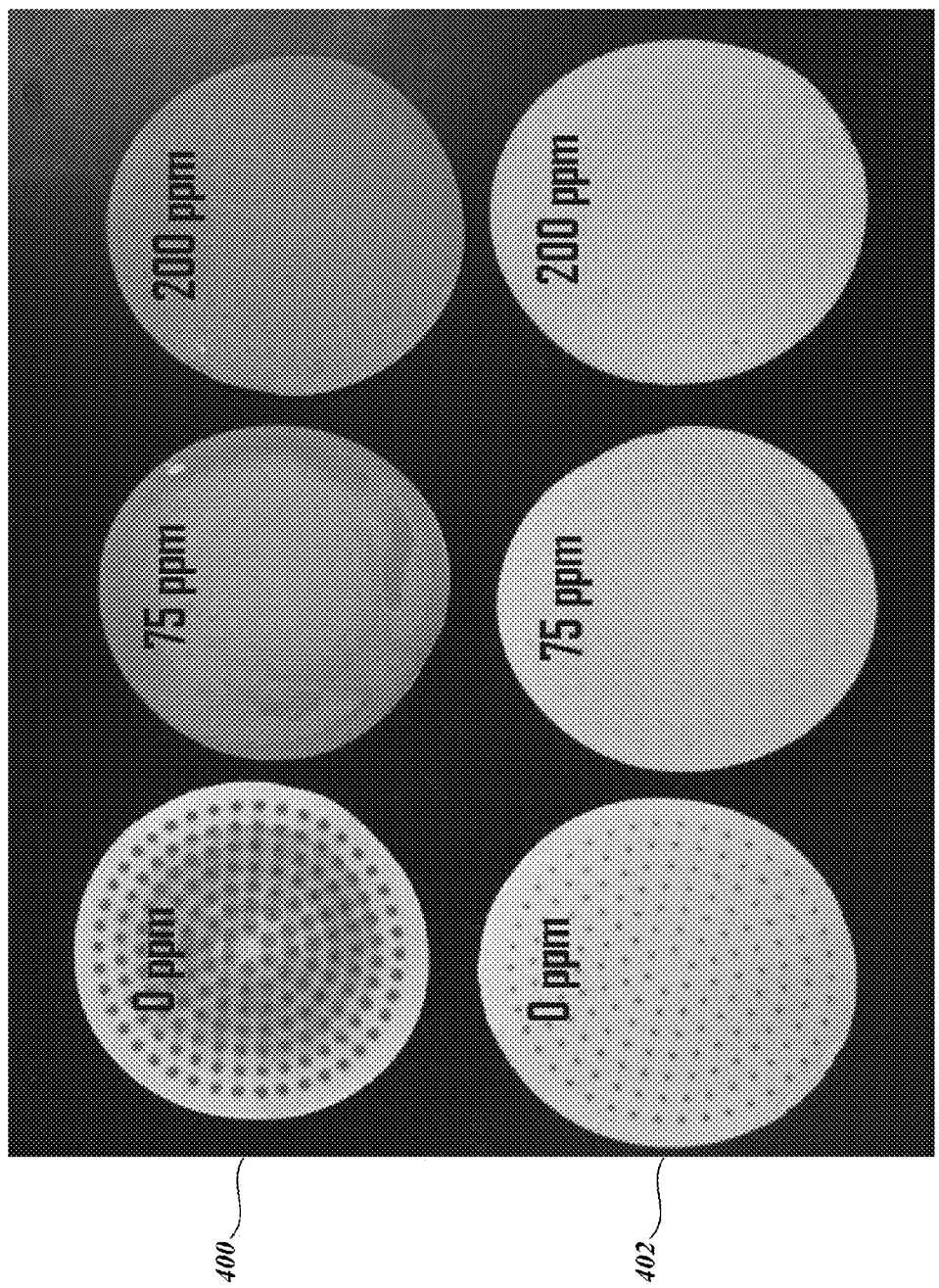
FIG. 8 is a photograph of samples of microalgae collected on filter papers, where the microalgae has been grown under dark and light conditions with varying amounts of chitosan.

Test 1: After 10 days, all jars were removed from the window sill. A visual comparison of the samples of different treatments is shown in FIG. 8.

The contents of each jar were individually mixed briefly on stir plates to dislodge any algae attached to the sides of the glass jars and suspend the algae to create a homogenous algal suspension for spectrophotometer analysis. One small sample was taken from each jar and placed in a cuvette and the absorbance measured at 600 nm and recorded in Tables 7 & 8.

Figure 9:
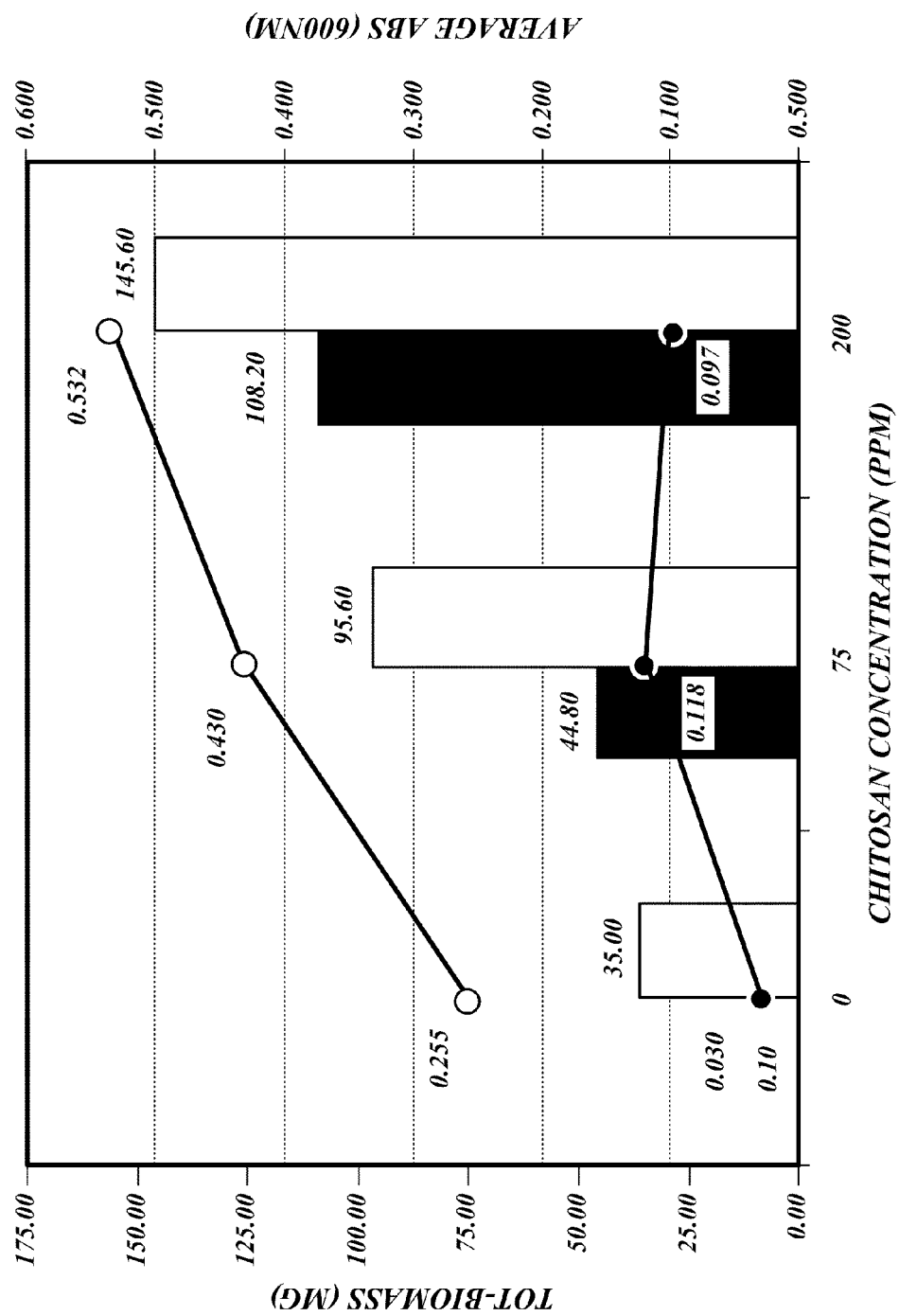
FIG. 9 is a graph representing the amount of microalgae growth by weight and absorbance of samples of microalgae grown under dark and light conditions with varying amounts of chitosan.

The measured absorbance (ABS) for each treatment group was used to calculate an average ABS for each specific treatment and used as an indicator of chlorophyll and photosynthetic pigments content. The average ABS data for light and dark conditions were plotted with their respective concentrations of chitosan in FIG. 9.

Results show that in the absence of light, chlorophyll and photosynthetic pigment content is greatly reduced with and without chitosan present. Light seems to be the driving factor in chlorophyll production. Although chlorophyll and photosynthetic pigment content in the algae suspensions grown in the dark was quite low compared to the algae suspensions grown in the light, it is possible that a significant amount of biomass still occurred in the dark. The presence of the white, near-transparent fluff in the dark containers could be algae growing without green pigments or chloroplasts. The growth of algae in the absence of photosynthesis is an indication that photosynthesis had been decoupled, possibly driven by the presence of chitosan and without the introduction of additional carbon-containing or protein-containing substances.

TABLE 7

Dark Sample Absorbance

| Sample | ABS 600 nm | Sample | ABS 600 nm | Sample | ABS 600 nm | Chitosan Conc. | Ave ABS |
|---|---|---|---|---|---|---|---|
| D1 | 0.028 | D2 | 0.118 | D5 | 0.082 | 0 | 0.030 |
| D4 | 0.031 | D3 | 0.114 | D7 | 0.086 | 75 | 0.118 |
| D8 | 0.032 | D6 | 0.122 | D9 | 0.124 | 200 | 0.097 |
|  | 0.030 |  | 0.118 |  | 0.097 |  |  |

TABLE 8

Light Sample Absorbance

| Sample | ABS 600 nm | Sample | ABS 600 nm | Sample | ABS 600 nm | Chitosan Conc. | Ave ABS |
|---|---|---|---|---|---|---|---|
| L2 | 0.254 | L5 | 0.44 | L1 | 0.536 | 0 | 0.255 |
| L4 | 0.266 | L7 | 0.426 | L3 | 0.513 | 75 | 0.430 |
| L9 | 0.245 | L8 | 0.425 | L6 | 0.546 | 200 | 0.532 |
|  | 0.255 |  | 0.430 |  | 0.532 |  |  |

Test 2: A Whatman glass fiber 1.6 um GF/A filter paper was assigned to each treatment jar, labeled, and dried in an oven at 55° C. for 1 day. Filter papers were weighed on an analytical balance and weights were recorded in Tables 9 & 10.

The entire contents of each jar were filtered through one of the filter papers by vacuum filtration using a Buchner funnel. After the contents in each jar were filtered, the filter paper was carefully removed and placed onto a glass dish. The filters were dried in an oven at 55° C. for 1 day, and the final weight of the dried filter papers+biomass were recorded in Tables 9 & 10. A set of the dried filter papers with the dried algae are shown in FIG. 8, wherein the samples that received light are the top row 400 and the samples in the dark are in the bottom row 402. The initial weight of the dried filter paper was then subtracted from the weight of the dried filter paper containing the dried biomass, and the difference was the dry biomass attributed to algal growth. The data is shown in Tables 9 & 10, and in FIG. 9 with their concentrations of chitosan.

Results show that in the absence of light, there remains a significant amount of algal growth in dark treatments containing 75 ppm and 200 ppm chitosan compared to the 0 ppm chitosan controls. There is also an increase in algal growth in algae suspensions grown in the light in the presence of 75 ppm and 200 ppm chitosan compared to the 0 ppm chitosan controls.

The results from this example suggest that photosynthesis-dependent growth may have been decoupled or overcome by the presence of chitosan. This is suggested because there was a significant increase in algal biomass in chitosan-containing algal suspensions grown in the absence of light without a significant increase or change in chlorophyll or photosynthetic pigment content within those same samples. The algae may have abandoned chlorophyll production in favor of chemotrophy. There was some aggregation of algae growth in the samples grown in the dark, but the time was not sufficient to show mat formation.

TABLE 9

Dark Sample Biomass Data

| Sample | Dried Filter | Volume Mass | Dried Filter + Biomass | Dry Biomass |
|---|---|---|---|---|
| D1 | 0.3414 | 196.26 | 0.3413 | −0.0000 |
| D4 | 0.3351 | 196.08 | 0.3343 | −0.0008 |
| D8 | 0.3344 | 190.96 | 0.3354 | 0.0010 |
|  |  | 194.4333 |  | 0.0000 |
| D2 | 0.3362 | 191.47 | 0.3531 | 0.0169 |
| D3 | 0.3383 | 197.06 | 0.3497 | 0.0114 |
| D6 | 0.3346 | 196.31 | 0.3511 | 0.0165 |
|  |  | 194.9467 |  | 0.0448 |
| D5 | 0.6677 | 198.43 | 0.6963 | 0.0286 |
| D7 | 1.3394 | 198.51 | 1.3811 | 0.0417 |
| D9 | 0.6714 | 200.23 | 0.7093 | 0.0379 |
|  |  | 199.0567 |  | 0.1082 |

TABLE 10

Light Sample Biomass Data

| Sample | Dried Filter | Volume Mass | Dried Filter + Biomass | Dry Biomass |
|---|---|---|---|---|
| L2 | 0.3362 | 196.35 | 0.3490 | 0.0128 |
| L4 | 0.3342 | 196.83 | 0.3454 | 0.0112 |
| L9 | 0.3340 | 197.66 | 0.3450 | 0.0110 |
|  |  | 196.9467 |  | 0.0350 |
| L5 | 0.6657 | 197.61 | 0.6995 | 0.0338 |
| L7 | 0.3351 | 196.74 | 0.3671 | 0.0320 |
| L8 | 0.3324 | 195.81 | 0.3622 | 0.0298 |
|  |  | 196.72 |  | 0.0956 |
| L1 | 0.3385 | 198.53 | 0.3893 | 0.0508 |
| L3 | 0.3331 | 199.97 | 0.3740 | 0.0409 |
| L6 | 0.3340 | 200.54 | 0.3879 | 0.0539 |
|  |  | 199.68 |  | 0.1456 |

Example 5

Increasing the Lipid Content Per Unit Mass of Algae Grown with Chitosan

Equal aliquots of a growing Green algae suspension containing algae in DI water that was prepared by spiking 3.6 L of DI water with 4 ml of a stock macronutrient concentrate and 4 ml of stock micronutrient concentrate, found in Table 11 & 12 below, was added to 4 separate vessels.

TABLE 11

Macronutrients (Adjusted to pH-7.5)

| Macronutrient | Concentrate (g/L) | Target in Final Solution (mg/L) |
|---|---|---|
| CaCl2*2H2O | 4.41 | 4.41 |
| K2HPO4 | 1.044 | 1.044 |
| MgCl2 | 5.7 | 5.7 |
| MgSO4*7H2O | 14.7 | 14.7 |
| NaHCO3 | 15 | 30* |
| NaNO3 | 1.044 | 1.044 |

TABLE 12

Micronutrients (Adjusted to pH-7.5)

| Micronutrient | Concentrate (g/L) | Target in Final Solution (mg/L) |
|---|---|---|
| CoCl2*2H2O | 0.001428 | 0.001428 |
| CuCl2*2H2O | 0.000012 | 0.000012 |
| FeCl3*6H2O | 0.16 | 0.16 |
| H3BO3 | 0.1855 | 0.1855 |
| MnCl2*4H2O | 0.4154 | 0.4154 |
| Na2EDTA*2H2O | 0.3 | 0.3 |
| Na2MoO4*2H2O | 0.00726 | 0.00726 |

*Additional NaHCO$_3$ was added to the final solution to raise the TOT-CO$_3$ concentration.

In addition to the listed ingredients, the water in two of the vessels contained chitosan at a concentration of 200 mg/L that was added to each vessel from a stock solution of chitosan acetate prepared by dissolving 1.00 gram of chitosan in 98.00 grams of water and 1.00 gram of glacial acetic acid. One of the vessels containing chitosan and another vessel containing only the macro and micro nutrients listed were both placed in the dark at ambient temperature for a period of 15 days. Another vessel containing chitosan and another vessel containing only the macro and micro nutrient ingredients were placed next to a window exposed to daylight at ambient temperature for the same number of days. After 15 days, all of the algae in each vessel was collected by centrifugation and then frozen and lyophilized to dryness and weighed. All of the dry algae from each vessel was extracted twice with isopropanol/hexane (2:3) using a tissue homogenizer to extract the algal lipids. The isopropanol/hexane extract from each isolate was filtered through a 1.6 micron glass fiber filter to remove insoluble algal debris and the filtrate containing the solvent-soluble lipids was heated to evaporate the isopropanol/hexane solvent leaving behind the isolated lipids contained in tared glass vials. The lipids from each isolate were then weighed. Results are shown in the Table 13 below.

TABLE 13

Lipid Content

| Sample Description | Total Recovered Dry Biomass (mg) | Total Extracted Lipids (mg) | Percent Recovered Lipids (wt. percent) |
|---|---|---|---|
| Control - grown in light | 105 | 5 | 4.8% |
| 200 ppm chitosan grown in light | 567 | 18 | 3.2% |
| Control - grown in dark | 9 | 0 | 0% |
| 200 ppm chitosan grown in dark | 87 | 1 | 1.1% |

Growth in the presence of chitosan resulted in an increased biomass compared to algae grown in the absence of chitosan. The effect of chitosan was observed for algae grown in daylight and as well as for algae grown in the absence of light. The recovered lipids were also increased in algae grown in the presence of chitosan and light. The amount of lipids extracted from the algae grown in the dark without chitosan was below the level of sensitivity of the analytical balance but was visibly present in the glass vial.

Example 6

Figure 10:
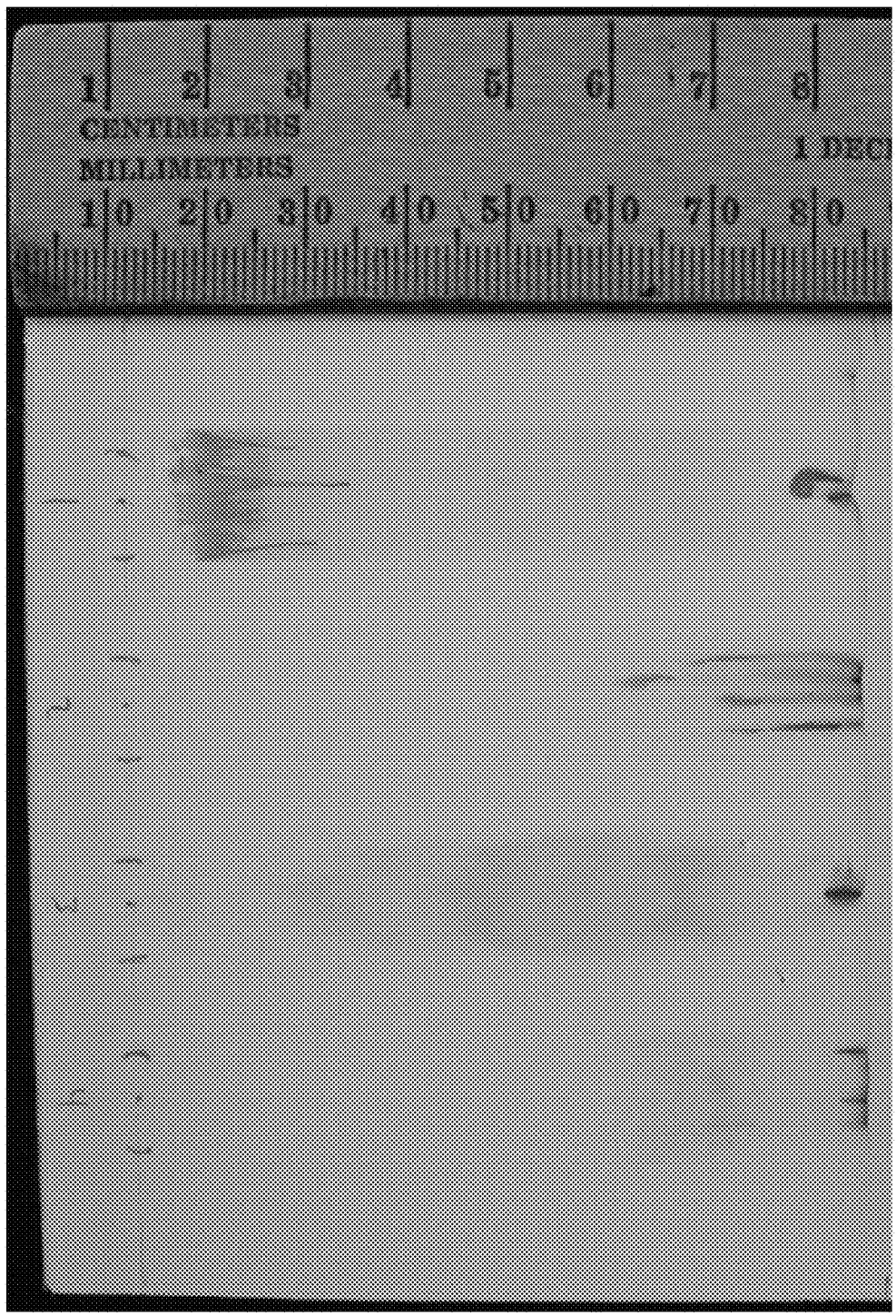
FIG. 10 is a photograph of a thin layer chromotography plate showing the lipid profiles of algae grown under light and dark conditions with and without chitosan.

Thin Layer Chromatography of Lipid Extracts from Algae Grown in the Absence or Presence of Chitosan Lipids isolated from the previous Example 5 that examined lipid yield were dissolved in a mixed solvent consisting of chloroform and methanol in a ratio of 2 volumes of chloroform to one volume of methanol. The amount of solvent used for each lipid extract was adjusted to provide approximately equal concentrations of lipid extract for each sample equaling a concentration of approximately 2 µg of lipid extract per µl of solvent. Lipid extracts were applied in a 1 cm wide line onto a silica plate and allowed to dry. As seen in FIG. 10, Lane 1: lipid extract from algae grown in daylight in 200 ppm chitosan; Lane 2: lipid extract from algae grown in daylight in the absence of chitosan; Lane 3; lipid extract from algae grown in the dark in 200 ppm chitosan; and Lane 4; lipid extract from algae grown in the dark in the absence of chitosan.

The thin layer chromatography plate containing the dried applied lipid extracts was placed in a solvent tank containing the development solvent consisting of chloroform, methanol and water in a ratio of 30 volumes of chloroform to 40 volumes of methanol to 10 volumes of water. The solvent front was allowed to migrate to the top of the TLC plate (~8.4 cm) in approximately 37 minutes. The TLC plate was removed and dried and placed in a sealed container containing iodine to allow the visualization of the separated lipids from each algae extract. As can be seen in FIG. 10, the lipid extract from algae grown in daylight in the presence of 200 ppm chitosan (lane 1) exhibits a different lipid profile compared to the lipid extract from algae grown in daylight in the absence of chitosan. There is a significant quantity of lipids concentrated near the application point from algae grown in the presence of chitosan that is absent from the lipid extract isolated from algae grown in the absence of chitosan (compare lane 1 with lane 2). In contrast, there is more concentrated population of lipids migrating at the top near the solvent front from algae grown in daylight in the absence of chitosan (compare lane 2 with lane 1). This demonstrates that the lipid profile in algae grown in daylight is influenced or changed by growth in the presence of chitosan. This effect is also observed for algae grown in the dark in the presence of chitosan. In lane 3, there is a smear of lipids (from algae grown in the presence of chitosan) that migrates about halfway between the top and bottom of the TLC plate that is absent from the lipid extract obtained from algae grown in the dark in absence of chitosan (compare lane 3 with lane 4). This demonstrates that the algae lipid profile can be influenced or changed by growth in the presence of chitosan in the dark, absent photosynthesis. Interestingly, the lipid profile is different between algae grown in daylight in the presence of chitosan compared to algae grown in the dark in the presence of chitosan. This suggests that the lipid species or profile can be altered or influenced by selecting growth conditions (light exposure vs. dark) in the presence of chitosan. The effect of chitosan may be advantageous to encourage the formation of desired lipids useful for certain applications particularly biofuel species. It is also possible that this data indicates that some other non-lipid components (soluble and extractable with hexane isopropanol mixed solvent) can be changed or their synthesis influenced by growth of algae in the presence of chitosan.

The embodiments of the invention in which an exclusive property or privilege is claimed are defined as follows:

1. A method for growing microalgae, comprising:
   introducing an amount of chitosan to an aqueous environment suited for growing microalgae;
   cultivating microalgae in the environment in the presence of chitosan over a period of time; and
   increasing microalgae growth with chitosan in comparison to microalgae growth without chitosan.

2. The method of claim 1, wherein microalgae growth is increased by at least 5% by weight as compared to microalgae growth without chitosan.

3. The method of claim 1, wherein microalgae growth is increased by at least 10% by weight as compared to microalgae growth without chitosan.

4. The method of claim 1, wherein microalgae growth is increased by at least 18% by weight as compared to microalgae growth without chitosan.

5. The method of claim 1, wherein microalgae growth is increased by at least 400% by weight as compared to microalgae growth without chitosan.

6. The method of claim 1, wherein the microalgae growth is aggregated by the chitosan.

7. The method of claim 1, wherein the microalgae is selected from at least one of a diatom, Green algae, Golden-brown algae, Blue Green algae, Prymnesiophyte or Eustigmatophyte.

8. The method of claim 1, wherein the microalgae comprises lipids.

9. The method of claim 1, further comprising draining the aqueous environment of water to harvest the microalgae.

10. The method of claim 1, further comprising cultivating the microalgae in a porous containment device that is transportable within the aqueous environment.

11. The method of claim 1, further comprising processing the microalgae into fuel.

12. The method of claim 1, wherein the amount of chitosan is approximately 25 ppm to 100 ppm.

13. The method of claim 1, wherein the amount of chitosan is approximately 150 ppm to 250 ppm.

14. The method of claim 1, wherein the amount of chitosan is greater than 250 ppm.

15. The method of claim 1, further comprising introducing a soluble anionic polymer to the aqueous environment.

16. The method of claim 1, further comprising introducing at least one of alginate, carageenan, xanthan gum, and anionic polyacrylamide to the environment.

17. The method of claim 1, wherein the aqueous environment comprises a raceway pond having one or more holes on the bottom thereof to drain water.

18. The method of claim 1, further comprising reducing or eliminating a source of light from the environment.

19. The method of claim 1, further comprising reducing or eliminating a source of light from the environment without introduction of carbon-containing, except for the chitosan, or protein-containing materials that cause the microalgae to grow.

20. The method of claim 1, wherein cultivating comprises at least one step selected from the group consisting of: introducing water to the aqueous environment, introducing nutrients to the aqueous environment, controlling the salinity of the aqueous environment, controlling the pH of the aqueous environment, and exposing the aqueous environment to a source of light.

21. The method of claim 1, comprising allowing time to grow the microalgae into one or a plurality of microalgae mats.

22. The method of claim 1, further comprising assigning carbon credits to carbon dioxide consumed by the microalgae as a result of the increase in growth of the microalgae grown in the presence of chitosan.

23. A method for growing microalgae, comprising:
introducing an amount of chitosan to an aqueous environment suited for growing microalgae;
cultivating microalgae in the environment in the presence of chitosan over a period of time; and
producing aggregated microalgae in the aqueous environment.

24. The method of claim 22, further comprising harvesting the aggregated microalgae.

25. The method of claim 22, wherein the microalgae is selected from at least one of a diatom, Green algae, Blue Green algae, Golden-brown algae, Prymnesiophyte, or Eustigmatophyte.

26. The method of claim 22, further comprising growing the microalgae into mats.

27. The method of claim 22, further comprising draining the aqueous environment of water to harvest the microalgae.

28. The method of claim 22, further comprising cultivating the microalgae in a porous containment device that is transportable within the aqueous environment.

29. A method for increasing the lipid content of microalgae, comprising:
introducing an amount of chitosan to an aqueous environment suited for growing microalgae;
providing microalgae to the environment, wherein the algae microalgae has an initial lipid content per unit mass of microalgae;
cultivating the microalgae in the environment in the presence of chitosan over a period of time; and
increasing the lipid content per unit mass of microalgae grown with chitosan as compared to the initial lipid content of the microalgae.

30. The method of claim 28, further comprising reducing or eliminating a source of light from the environment.

31. A method for altering the lipid profile of microalgae, comprising:
introducing an amount of chitosan to an aqueous environment suited for growing microalgae;
providing microalgae to the environment, wherein the microalgae has an initial lipid profile comprising a plurality of lipid species;
cultivating the microalgae in the environment in the presence of chitosan over a period of time; and
altering the lipid profile of microalgae grown with chitosan as compared to the initial lipid profile of microalgae.

32. The method of claim 30, further comprising reducing or eliminating a source of light from the environment.

33. A method for removing constituents from water, comprising:
introducing chitosan to an aqueous environment suited for growing microalgae, wherein the environment contains constituents desired to be removed;
cultivating microalgae in the environment in the presence of chitosan over a period of time, wherein the constituents are taken up by the microalgae; and
harvesting the microalgae to remove the constituents from the water.

* * * * *

UNITED STATES PATENT AND TRADEMARK OFFICE
CERTIFICATE OF CORRECTION

Page 1 of 1

PATENT NO.           : 8,281,515 B2
APPLICATION NO.      : 12/824948
DATED                : October 9, 2012
INVENTOR(S)          : E. J. Nichols et al.

It is certified that error appears in the above-identified patent and that said Letters Patent is hereby corrected as shown below:

IN THE CLAIMS

| COLUMN | LINE | ERROR |
|---|---|---|
| 21 (Claim 29, line 6) | 32 | before "microalgae", delete "algae" |

Signed and Sealed this
Twenty-fourth Day of September, 2013

Teresa Stanek Rea
*Deputy Director of the United States Patent and Trademark Office*

UNITED STATES PATENT AND TRADEMARK OFFICE
CERTIFICATE OF CORRECTION

PATENT NO. : 8,281,515 B2  
APPLICATION NO. : 12/824948  
DATED : October 9, 2012  
INVENTOR(S) : E. J. Nichols et al.

Page 1 of 1

It is certified that error appears in the above-identified patent and that said Letters Patent is hereby corrected as shown below:

In the Claims

| COLUMN | LINE | ERROR |
|---|---|---|
| 21 (Claim 24, line 1) | 14 | "claim 22," should read --claim 23-- |
| 21 (Claim 25, line 1) | 16 | "claim 22," should read --claim 23-- |
| 21 (Claim 26, line 1) | 20 | "claim 22," should read --claim 23-- |
| 21 (Claim 27, line 1) | 22 | "claim 22," should read --claim 23-- |
| 21 (Claim 28, line 1) | 24 | "claim 22," should read --claim 23-- |
| 22 (Claim 30, line 1) | 6 | "claim 28," should read --claim 29-- |
| 22 (Claim 32, line 1) | 19 | "claim 30," should read --claim 31-- |

Signed and Sealed this  
Thirtieth Day of September, 2014

Michelle K. Lee  
*Deputy Director of the United States Patent and Trademark Office*